United States Patent
Kobayashi (10) Patent No.: US 11,892,575 B2
(45) Date of Patent: Feb. 6, 2024

(54) RADIATION IMAGING APPARATUS, DATA PROCESSING APPARATUS, RADIATION IMAGING SYSTEM, AND CONTROL METHOD FOR RADIATION IMAGING SYSTEM

(71) Applicant: CANON KABUSHIKI KAISHA, Tokyo (JP)

(72) Inventor: Shigeo Kobayashi, Kanagawa (JP)

(73) Assignee: Canon Kabushiki Kaisha, Tokyo (JP)

(\*) Notice: Subject to any disclaimer, the term of this patent is extended or adjusted under 35 U.S.C. 154(b) by 189 days.

(21) Appl. No.: 17/681,613

(22) Filed: Feb. 25, 2022

(65) Prior Publication Data
US 2022/0276397 A1 Sep. 1, 2022

(30) Foreign Application Priority Data
Mar. 1, 2021 (JP) .................. 2021-031423

(51) Int. Cl.
*G01T 1/24* (2006.01)
*A61B 6/00* (2006.01)

(52) U.S. Cl.
CPC .............. *G01T 1/247* (2013.01); *A61B 6/563* (2013.01); *G01T 1/244* (2013.01)

(58) Field of Classification Search
CPC .......... A61B 6/563; G01T 1/244; G01T 1/247
See application file for complete search history.

(56) References Cited

U.S. PATENT DOCUMENTS

| | | | | |
|---|---|---|---|---|
| 2009/0034683 A1* | 2/2009 | Tamakoshi | ............. | G03B 42/02 378/91 |
| 2010/0208871 A1* | 8/2010 | Tanabe | .................. | A61B 6/548 378/189 |
| 2010/0246757 A1* | 9/2010 | Liu | ........................ | G03B 42/02 378/19 |
| 2013/0010928 A1* | 1/2013 | Hannon | .................. | A61B 6/56 378/98 |
| 2015/0327833 A1* | 11/2015 | Tsuchiya | .............. | A61B 6/4405 378/91 |
| 2016/0015354 A1* | 1/2016 | Exelmans | ............. | H04W 24/10 375/295 |
| 2016/0081639 A1* | 3/2016 | Bettouyashiki | ....... | A61B 6/4283 378/189 |
| 2017/0025761 A1* | 1/2017 | Kim | ..................... | A61B 6/4452 |

FOREIGN PATENT DOCUMENTS

JP 2010243486 A 10/2010

\* cited by examiner

*Primary Examiner* — Blake C Riddick
(74) *Attorney, Agent, or Firm* — Canon U.S.A., Inc., IP Division (57) ABSTRACT

A radiation imaging system includes a data processing apparatus and a radiation imaging apparatus. The radiation imaging apparatus includes a plurality of antennas for transmitting and receiving data to and from the data processing apparatus via wireless communication. The data processing apparatus transmits, to the radiation imaging apparatus, information about an antenna that is preset as an antenna to be used from among the plurality of antennas. The radiation imaging apparatus selects, based on the information, the antenna to be used from the plurality of antennas.

11 Claims, 8 Drawing Sheets

| RADIATION IMAGING APPARATUS | ANTENNA INITIAL VALUE |
|---|---|
| 101a | ANT_1 |
| 101b | ANT_2 |
| ⋮ | ⋮ |
| ⋮ | ⋮ |

| RADIATION IMAGING APPARATUS | ANTENNA INITIAL VALUE |
|---|---|
| 101a | ANT_1 |
| 101b | ANT_2 |
| ⋮ | ⋮ |
| ⋮ | ⋮ |

FIG.5

| RADIATION IMAGING APPARATUS | USE CONDITION | ANTENNA INITIAL VALUE |
|---|---|---|
| 101a | MOUNTED ON DECUBITUS POSITION-TYPE MOUNT 102 | ANT_1 |
| 101a | MOUNTED ON ERECT POSITION-TYPE MOUNT 110 | ANT_2 |
| 101b | MOUNTED ON DECUBITUS POSITION-TYPE MOUNT 102 | ANT_1 |
| 101b | MOUNTED ON ERECT POSITION-TYPE MOUNT 110 | ANT_1 |
| ⋮ | ⋮ | ⋮ |

| | RADIATION IMAGING APPARATUS | USE CONDITION | ANTENNA INITIAL VALUE |
|---|---|---|---|
| RADIATION IMAGING SYSTEM 601 | 101a | MOUNTED ON DECUBITUS POSITION-TYPE MOUNT 102 | ANT_1 |
| | 101a | MOUNTED ON ERECT POSITION-TYPE MOUNT 110 | ANT_2 |
| | 101b | MOUNTED ON DECUBITUS POSITION-TYPE MOUNT 102 | ANT_1 |
| | 101b | MOUNTED ON ERECT POSITION-TYPE MOUNT 110 | ANT_1 |
| | ⋮ | ⋮ | ⋮ |
| | RADIATION IMAGING APPARATUS | USE CONDITION | ANTENNA INITIAL VALUE |
| RADIATION IMAGING SYSTEM 602 | 101a | MOUNTED ON DECUBITUS POSITION-TYPE MOUNT 102 | ANT_1 |
| | 101a | MOUNTED ON ERECT POSITION-TYPE MOUNT 110 | ANT_2 |
| | 101a | MOUNTED ON ERECT POSITION-TYPE MOUNT 110a | ANT_1 |
| | 101b | MOUNTED ON DECUBITUS POSITION-TYPE MOUNT 102 | ANT_1 |
| | 101b | MOUNTED ON ERECT POSITION-TYPE MOUNT 110 | ANT_1 |
| | 101b | MOUNTED ON ERECT POSITION-TYPE MOUNT 110a | ANT_2 |
| | ⋮ | ⋮ | ⋮ |

RADIATION IMAGING APPARATUS, DATA PROCESSING APPARATUS, RADIATION IMAGING SYSTEM, AND CONTROL METHOD FOR RADIATION IMAGING SYSTEM

BACKGROUND

Field

The present disclosure relates to a radiation imaging apparatus, a data processing apparatus, a radiation imaging system, and a method for controlling the radiation imaging system.

Description of the Related Art

The widespread use of radiation imaging apparatuses that capture digital radiation images based on emitted radiation has promoted the digitization of radiation imaging systems. The digitization of the radiation imaging systems has allowed the images to be confirmed immediately after radiation imaging, thereby contributing to significant improvement of the workflow, compared to conventional imaging using films and imaging using computed radiography (CR) apparatuses. In recent years, wirelessly communicable radiation imaging apparatuses have further improved the convenience of radiation imaging apparatuses.

As an example of a wirelessly communicable radiation imaging apparatus, Japanese Patent Application Laid-Open No. 2010-243486 discusses a radiation imaging apparatus equipped with a plurality of antennas for wireless communication. The radiation imaging apparatus discussed in Japanese Patent Application Laid-Open No. 2010-243486 is capable of selecting an antenna to be used from the plurality of wireless communication antenna, based on a measurement result of communication strength of each of the plurality of wireless communication antennas.

Controlling the selection based on the measurement result of the communication strength, as discussed in Japanese Patent Application Laid-Open No. 2010-243486, can result in unnecessary selection control depending on the environment where the radiation imaging apparatus is installed, thereby leading to reduced imaging efficiency.

SUMMARY

The present disclosure is directed to providing a radiation imaging system that uses a radiation imaging apparatus configured to select an antenna to be used from a plurality of antennas for wireless communication, and that efficiently controls the selection.

According to an aspect of the present disclosure, a radiation imaging system includes a data processing apparatus, and a radiation imaging apparatus including a plurality of antennas for performing, via wireless communication, at least one of reception of control data from the data processing apparatus or transmission of radiation image data to the data processing apparatus, wherein the radiation image data is acquired by an imaging operation performed based on the control data and with respect to emitted radiation. The data processing apparatus transmits, to the radiation imaging apparatus, information about an antenna that is preset as an antenna to be used from among the plurality of antennas. The radiation imaging apparatus selects, based on the information, the antenna to be used from the plurality of antennas.

According to another aspect of the present disclosure, a method for controlling a radiation imaging system including a data processing apparatus and a radiation imaging apparatus, the radiation imaging apparatus including a plurality of antennas for performing, via wireless communication, at least one of reception of control data from the data processing apparatus or transmission of radiation image data to the data processing apparatus, the radiation image data being acquired by an imaging operation performed based on the control data and with respect to emitted radiation includes causing the data processing apparatus to transmit, to the radiation imaging apparatus, information about an antenna that is preset as an antenna to be used from among the plurality of antennas, and causing the radiation imaging apparatus to select, based on the information, the antenna to be used from the plurality of antennas.

According to yet another aspect of the present disclosure, a radiation imaging apparatus including a plurality of antennas for performing, via wireless communication, at least one of reception of control data from a data processing apparatus or transmission of radiation image data to the data processing apparatus, the radiation image data being acquired by an imaging operation performed based on the control data and with respect to emitted radiation includes a communication unit configured to receive information about an antenna that is preset as an antenna to be used from among the plurality of antennas, the information being transmitted from the data processing apparatus, and a selection unit configured to select, based on the information, the antenna to be used from the plurality of antennas.

According to yet another aspect of the present disclosure, a data processing apparatus configured to transmit control data to and receive radiation image data from a radiation imaging apparatus via wireless communication, the radiation imaging apparatus including a plurality of antennas for performing, via the wireless communication, at least one of reception of the control data or transmission of the radiation image data to the data processing apparatus, the radiation image data being acquired by an imaging operation performed based on the control data and with respect to emitted radiation includes a storage unit storing information about an antenna that is preset as an antenna to be used from among the plurality of antennas. The data processing apparatus transmits the information to the radiation imaging apparatus.

Further features will become apparent from the following description of exemplary embodiments with reference to the attached drawings.

DESCRIPTION OF THE EMBODIMENTS

Exemplary embodiments will be described with reference to the attached drawings. The exemplary embodiments described below are not intended to be limiting. All of a plurality of features described in the exemplary embodiments are not necessarily essential to implementing the exemplary embodiments and the plurality of features can be combined as appropriate. The same or similar configurations are denoted by the same reference numerals in the attached drawings, and redundant descriptions thereof will be omitted. Radiation according to the exemplary embodiments includes, for example, α rays, β rays, and γ rays, which are beams generated by particles (including photons) emitted by radioactive decay, and also include beams having an equivalent or higher degree of energy, such as X-rays, particle rays, and cosmic rays.

Figure 1:
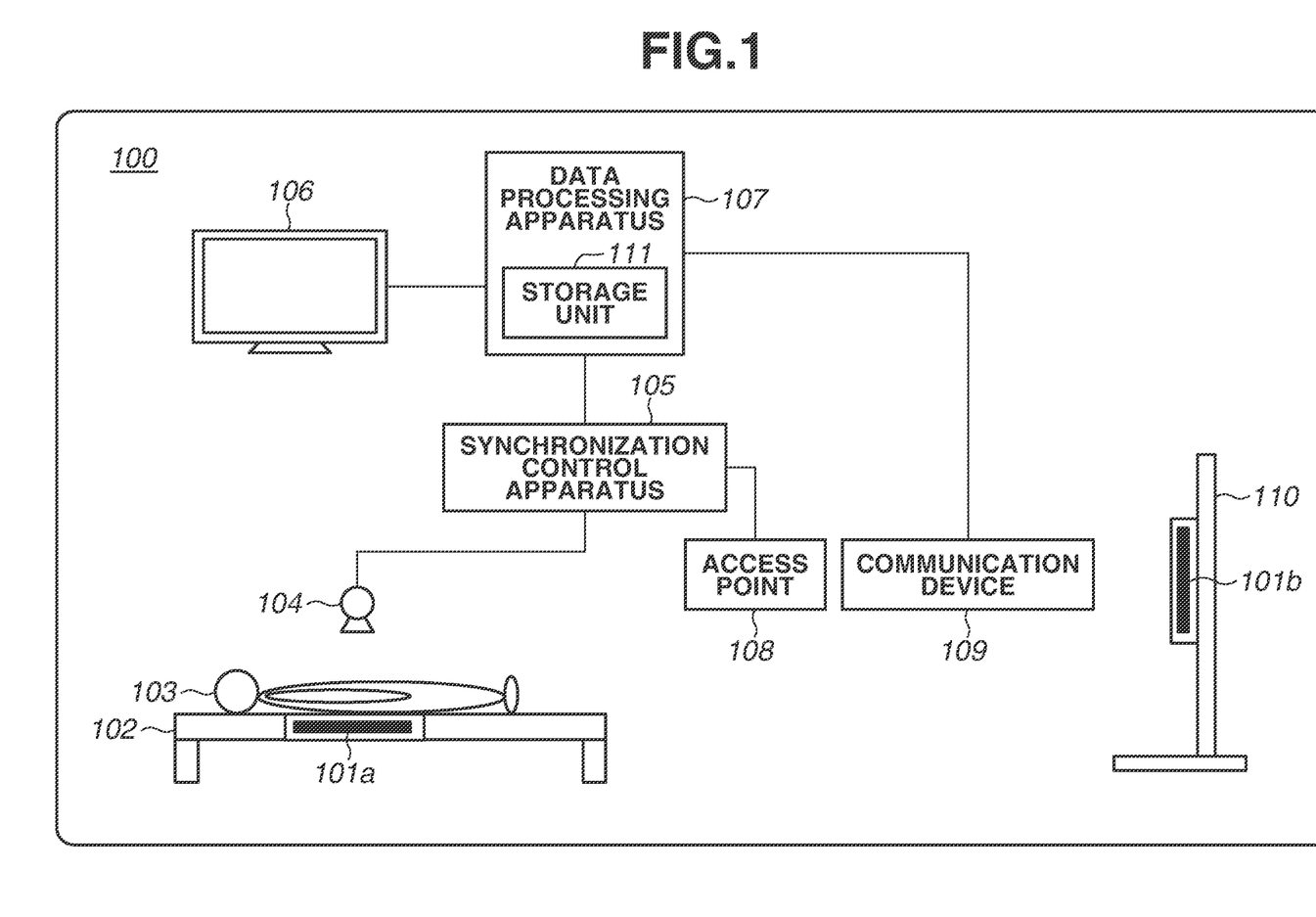
FIG. 1 is a block diagram illustrating a configuration of a radiation imaging system according to a first exemplary embodiment.

A radiation imaging system 100 according to a first exemplary embodiment will be described with reference to FIGS. 1 to 4. FIG. 1 is a block diagram illustrating a configuration of the radiation imaging system 100 according to the present exemplary embodiment. The radiation imaging system 100 includes radiation imaging apparatuses 101a and 101b, a decubitus position-type mount 102, a radiation generation apparatus 104, a synchronization control apparatus 105, a display apparatus 106, a data processing apparatus 107, an access point 108, a communication device 109, and an erect position-type mount 110.

The radiation imaging apparatus 101a and the radiation imaging apparatus 101b are installed on the decubitus position-type mount 102 and the erect position-type mount 110, respectively, and acquire radiation images by performing imaging with respect to radiation emitted from the radiation generation apparatus 104 and transmitted through a subject 103. The decubitus position-type mount 102 is a mount on which the radiation imaging apparatus 101a or the radiation imaging apparatus 101b is placed when the subject 103, in a decubitus position, is imaged. The erect position-type mount 110 is a mount on which the radiation imaging apparatus 101a or the radiation imaging apparatus 101b is placed when the subject 103, in an erect position, is imaged.

The data processing apparatus 107 receives a radiation image captured by each of the radiation imaging apparatuses 101a and 101b, performs image processing on the received radiation image, and controls display of the processed radiation image on the display apparatus 106. The data processing apparatus 107 also transmits imaging conditions input via an operation unit (not illustrated) to at least one of the radiation imaging apparatus 101a or the radiation imaging apparatus 101b. The data processing apparatus 107 also transmits setting information, which enables the radiation imaging apparatuses 101a and 101b and the data processing apparatus 107 to wirelessly communicate with each other, to at least one of the radiation imaging apparatus 101a or the radiation imaging apparatus 101b. More specifically, the radiation imaging apparatuses 101a and 101b perform at least one of reception of control data, such as the imaging conditions and the setting information, from the data processing apparatus 107 or transmission of radiation image data acquired by the imaging performed based on the control data to the data processing apparatus 107. The data processing apparatus 107 performs at least one of transmission of the control data to the radiation imaging apparatuses 101a and 101b or reception of the radiation image data from the radiation imaging apparatuses 101a and 101b. The transmission and reception described above are performed via wireless communication.

The access point 108 relays radio waves for exchanging information (data) via the wireless communication between the radiation imaging apparatuses 101a and 101b and the data processing apparatus 107. In a case where the radiation imaging apparatus 101a or 101b or the data processing apparatus 107 has an access point function, the access point 108 can be eliminated.

The communication device 109 is a transmitter and receiver of radio waves for performing short-range wireless communication between the radiation imaging apparatuses 101a and 101b and the data processing apparatus 107. For example, the communication device 109 is connectable to the data processing apparatus 107 via a Universal Serial Bus (USB) interface. Examples of the communication device 109 include a device supporting at least one of the Bluetooth® Basic Rate/Enhanced Data Rate (BR/EDR) standard and the Bluetooth® Low Energy (LE) standard. The communication device 109 can also be a Radio Frequency Identifier (RFID) device that exchanges information with a tag in which identification (ID) information is embedded, via short-range wireless communication using an electromagnetic field, radio waves, or the like. In this case, the RFID communication method can be any of the electromagnetic induction method or the radio wave method. A function built in another apparatus such as the radiation generation apparatus 104 can be used in place of the communication device 109.

The synchronization control apparatus 105 includes a circuit that mediates the communication and monitors the states of the radiation imaging apparatuses 101a and 101b and the radiation generation apparatus 104. The synchronization control apparatus 105 controls, for example, irradiation with the radiation from the radiation generation apparatus 104, and the imaging of the subject 103 by the radiation imaging apparatuses 101a and 101b. In addition, a hub (not illustrated) that connects a plurality of network devices can be built in the synchronization control apparatus 105. The synchronization control apparatus 105 can be configured integrally with the data processing apparatus 107, and may not necessarily be provided separately as long as the data processing apparatus 107 has the function of the synchronization control apparatus 105.

The radiation generation apparatus 104, for example, includes a radiation tube that accelerates electrons with a high voltage and causes the electrons to hit an anode in order to generate radiation such as X-rays.

Figure 2:
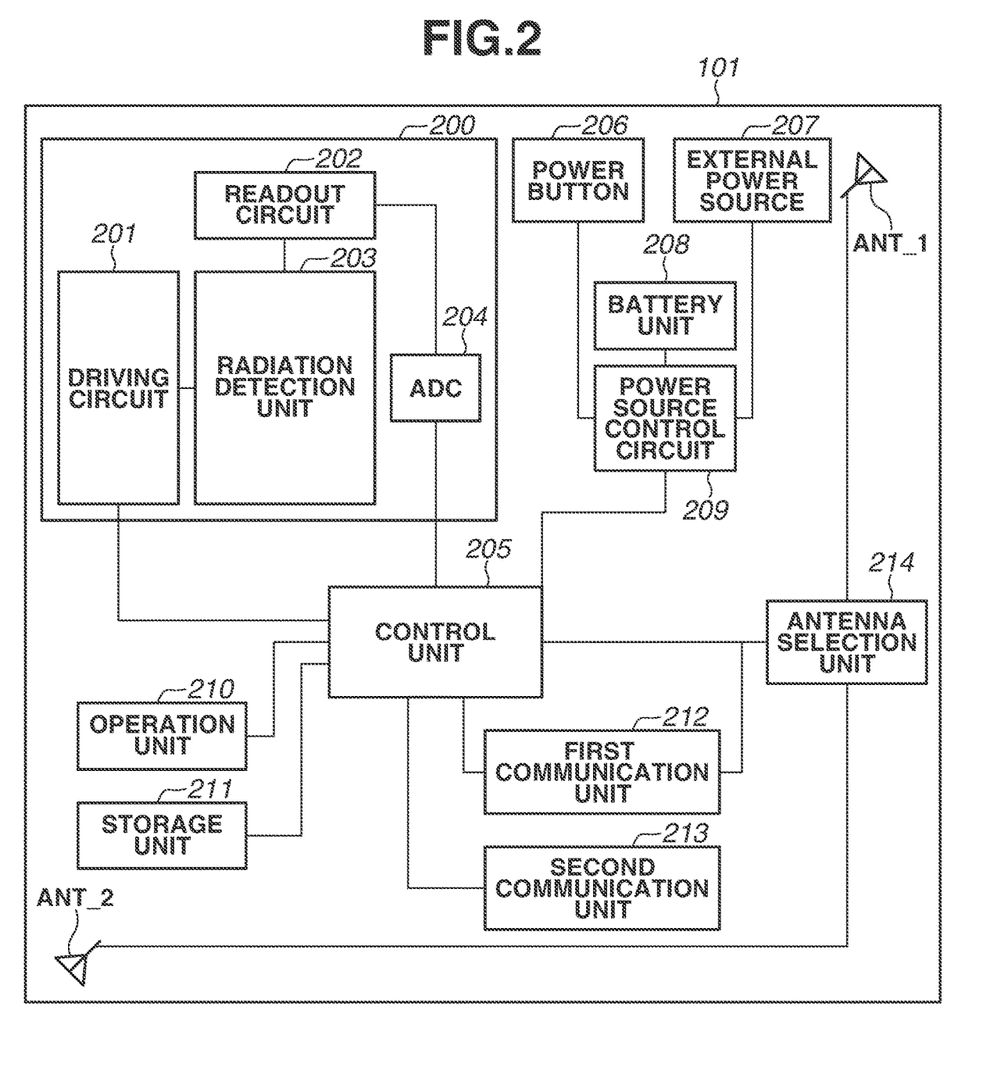
FIG. 2 is a schematic block diagram illustrating a configuration of main components of a radiation imaging apparatus according to the first exemplary embodiment.

Next, a configuration of main components of a radiation imaging apparatus 101 usable as each of the radiation imaging apparatuses 101a and 101b will be described with reference to FIG. 2. FIG. 2 is a schematic block diagram illustrating the configuration of the main components of the radiation imaging apparatus 101.

A power button 206 is an operation member for starting or stopping power supply to each component of the radiation imaging apparatus 101. A user operates the power button 206 to prepare for imaging.

A battery unit 208 supplies a predetermined voltage from a battery (not illustrated). For example, the battery unit 208 supplies power to a preparation operation detection unit (not illustrated) or the like. For example, a lithium ion battery or an electric double layer capacitor can be used as the battery. In a case where power is constantly supplied from an external power source, the battery unit 208 can be eliminated.

An external power source 207 supplies a predetermined voltage from an external power source. Generally, a wired power supply method is used, but a non-contact power supply and the like can also be used.

Based on the operation state of the power button 206, a power source control circuit 209, for example, controls power supply from each of the battery unit 208 and the external power source 207 to each component, and monitors the remaining battery amount via connections with the battery unit 208 and the external power source 207. For example, the power source control circuit 209 transforms the voltage from the battery unit 208 into a predetermined voltage and supplies the voltage to each component. For example, in a case where the external power source 207 is disconnected, pressing the power button 206 enables switching on or off the power supply from the battery unit 208.

A radiation imaging unit 200 includes a driving circuit 201, a readout circuit 202, a radiation detection unit 203, and an analog-to-digital converter (ADC) 204, and performs the imaging with respect to the emitted radiation to acquire the radiation image data. The radiation detection unit 203 detects the radiation transmitted through the subject 103 as an image signal (an electric charge). The radiation detection unit 203 includes a pixel array (not illustrated) in which a plurality of pixels (not illustrated) is arranged in a plurality of rows and a plurality of columns Each of the pixels includes a conversion element that converts the radiation into an electric charge, and a switch element that switches between accumulation and output of the electric signal corresponding to the electric charge. The conversion element includes, for example, a photoelectric conversion element and a scintillator that converts the radiation into light that the photoelectric conversion element can sense. The driving circuit 201 drives the radiation detection unit 203 by supplying a driving signal for driving a pixel to the radiation detection unit 203. The driving circuit 201 is an integrated circuit that causes the pixel to, for example, accumulate or output the electric signal corresponding to the electric charge. The readout circuit 202 is an integrated circuit that reads out the electric signal output from the pixel, and has a function of amplifying and reading out the output electric signal and a function of converting electric signals read out in parallel into electric signals in series. The ADC 204 has an analog-to-digital conversion function of converting the analog electric signal read out by the readout circuit 202 into digital data, and outputs the digital data as radiation image data. The radiation image data output from the ADC 204 is input to a control unit 205.

A storage unit 211 stores the radiation image data output from the ADC 204, a system identifier, a calculated distance threshold value calculated based on radio wave intensity between the radiation imaging apparatus 101 and the communication device 109, and an offset image. The storage unit 211 can also store a technician ID, which is identification information about a technician, a patient ID, which is identification information about a patient, an imaging time, an imaging radiation dose, an imaging region, the imaging conditions including the number of images to be captured, a transfer history of the radiation image data, and the like, which correspond to the generated image data, in association with one another. The storage unit 211 is a readable and writable device, and corresponds to a nonvolatile memory such as a flash memory. The storage unit 211 is however not limited thereto, and cam be a volatile storage device such as a static dynamic random access memory (SDRAM). The storage unit 211 can also be detachably mounted on the data processing apparatus 107, like a Secure Digital (SD) card.

A first communication unit 212 performs wireless communication with the data processing apparatus 107 or the synchronization control apparatus 105, and a wireless communication module is appropriately set depending on a medium used in the wireless communication. For example, the first communication unit 212 is communicable with the access point 108 via a wireless local area network (WLAN). For example, the first communication unit 212 receives the control data from the data processing apparatus 107 and transmits the radiation image data to the data processing apparatus 107 via the access point 108. A plurality of antennas ANT_1 and ANT_2 for the wireless communication is provided for the first communication unit 212.

A second communication unit 213 performs wireless communication with the data processing apparatus 107, and a wireless communication module is appropriately set depending on the medium used in the wireless communication. For example, the second communication unit 213 performs the short-range wireless communication with the communication device 109 via a wireless personal area network (WPAN). In other words, the wireless communication between the communication device 109 and the second communication unit 213 and the wireless communication between the data processing apparatus 107 and the first communication unit 212 are different from each other. The second communication unit 213 has a function of receiving antenna initial value information transmitted from the data processing apparatus 107. The antenna initial value information is information about one of the plurality of antennas ANT_1 and ANT_2 that is preset to be used. The second communication unit 213 also receives wireless communication setting information such as the identifier of the radiation imaging system 100, and a Service Set Identifier (SSID), an encryption key, and an Internet Protocol (IP) address that are used in communication with the first communication unit 212. The above-described information is stored in a storage unit 111 of the data processing apparatus 107 illustrated in FIG. 1, and transmitted to the second communication unit 213 via the communication device 109. The antenna initial value information will be described in detail below with reference to FIG. 3. An antenna selection unit (a selection unit) 214 selects the antenna to be used as a default antenna from the plurality of antennas ANT_1 and ANT_2 according to an instruction from the control unit 205, based on the antenna initial value information received by the second communication unit 213. The control unit 205 controls the components of the radiation imaging apparatus 101 for the imaging based on the control data received from the data processing apparatus 107.

An operation unit 210 can be used as a manual trigger for transmitting and receiving the setting information between the radiation imaging apparatus 101 and the communication device 109. For example, when the operation unit 210 is operated, the identifier of the radiation imaging system 100, and the antenna initial value information, the SSID, the encryption key, and the IP address that are set for the first communication unit 212 can be transmitted and received.

Figure 3:
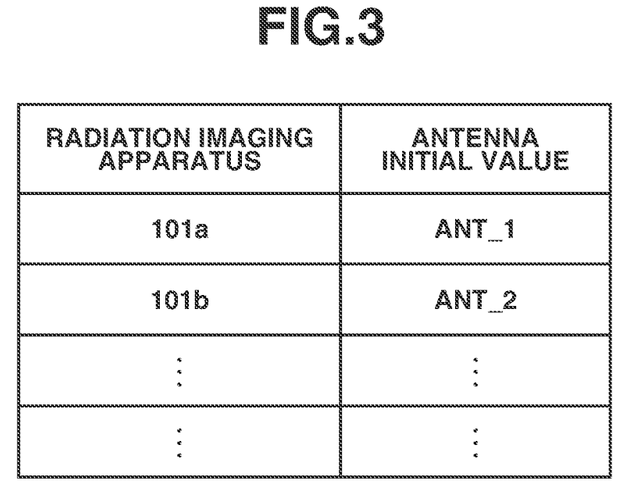
FIG. 3 is a schematic diagram illustrating an example of antenna initial value information according to the first exemplary embodiment.

Next, the antenna initial value information will be described with reference to FIG. 3. FIG. 3 is a schematic diagram illustrating an example of the antenna initial value information stored in the storage unit 111. As illustrated in FIG. 3, an initial setting antenna, which is preset to be used as the default antenna of the radiation imaging apparatus 101a, is the antenna ANT_1, and the initial setting antenna of the radiation imaging apparatus 101b is the antenna ANT_2. In other words, in the radiation imaging system 100 including the plurality of radiation imaging apparatuses 101a and 101b, the antenna initial value information is stored in the storage unit 111 for both of the radiation imaging apparatuses 101a and 101b. The antenna ANT_1 is preset as the antenna to be used for the radiation imaging apparatus 101a installed on the decubitus position-type mount 102. The antenna ANT_2 is preset as the antenna to be used for the radiation imaging apparatus 101b installed on the erect position-type mount 110. In other words, the antenna to be used is selected in advance for each of the radiation imaging apparatuses 101a and 101b depending on the installation condition. The antenna initial value information is transmitted to the radiation imaging apparatuses 101a and 101b via the communication device 109, together with the wireless communication setting information such as the identifier of the radiation imaging system 100, and the SSID, the encryption key, and the IP address that are for use in communication with the first communication unit 212. The antenna initial value information can be any information that enables identification of each of the plurality of antennas ANT_1 and ANT_2.

Figure 4:
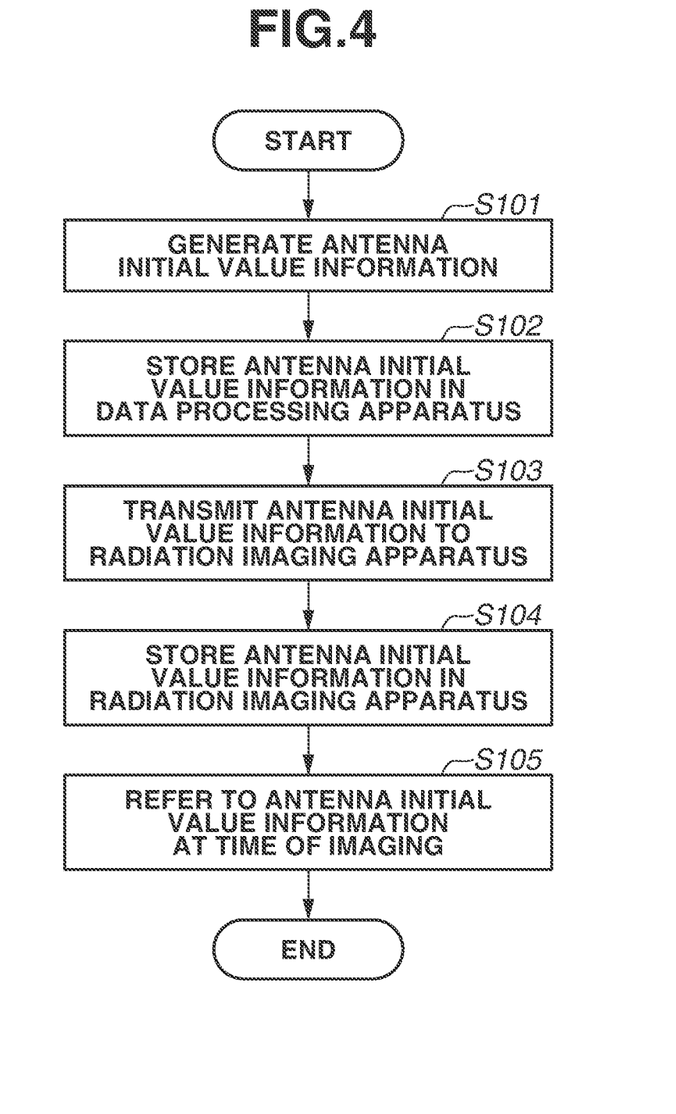
FIG. 4 is a flowchart illustrating selection control according to the first exemplary embodiment.

Next, selection control for selecting the antenna preset to be used for each of the radiation imaging apparatuses 101a and 101b including the plurality of antennas ANT_1 and ANT_2 in the radiation imaging system 100 will be described with reference to FIG. 4.

In step S101, the antenna initial value information illustrated in FIG. 3 is generated. In step S102, the antenna initial value information illustrated in FIG. 3 is stored in the storage unit 111 of the data processing apparatus 107. In step S103, the antenna initial value information is transmitted from the storage unit 111 of the data processing apparatus 107 to at least one of the radiation imaging apparatus 101a or the radiation imaging apparatus 101b. In step S104, the antenna initial value information received via the second communication unit 213 is stored in the storage unit 211. In step S105, the control unit 205 controls the antenna selection unit 214 based on the antenna initial value information stored in the storage unit 211, and the antenna selection unit 214 controlled by the control unit 205 selects the antenna corresponding to the antenna initial value information between the plurality of antennas ANT_1 and ANT_2.

As described above, the radiation imaging system 100 is configured such that the data processing apparatus 107 presets the antenna to be used (the initial antenna) between the plurality of antennas ANT_1 and ANT_2 for each of the radiation imaging apparatuses 101a and 101b. Thus, in the radiation imaging system 100 using the radiation imaging apparatuses 101a and 101b, each configured to select the antenna to be used between the plurality of antennas ANT_1 and ANT_2 for wireless communication, it is possible to efficiently control the selection without relying on the measurement result of the communication strength.

Figure 5:
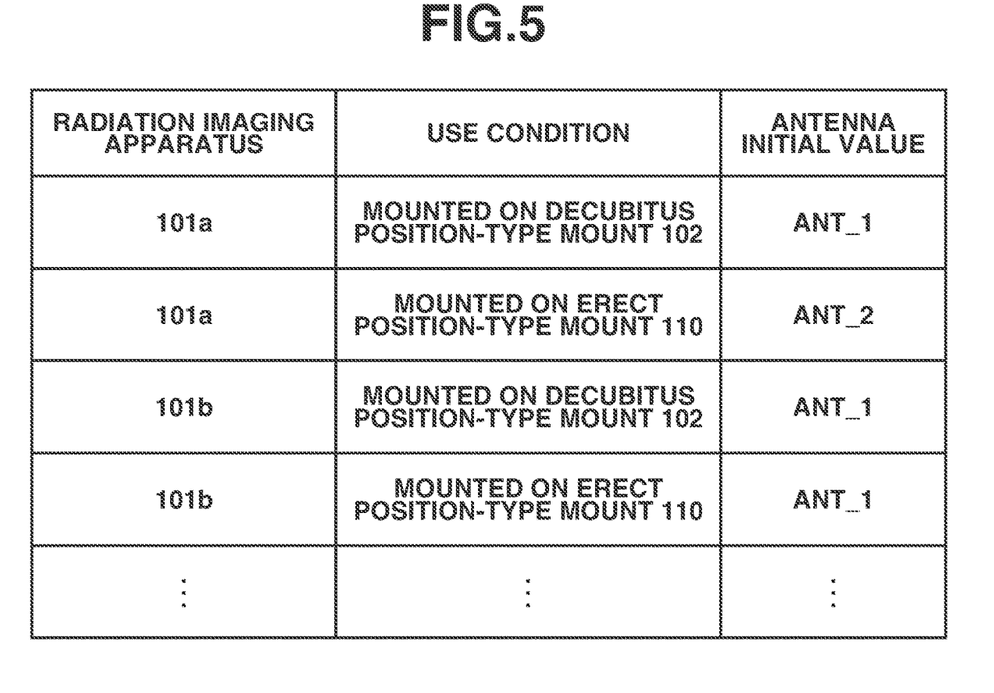
FIG. 5 is a schematic diagram illustrating an example of antenna initial value information according to a second exemplary embodiment.

Next, a second exemplary embodiment will be described with reference to FIG. 5. In the present exemplary embodiment, a case where both of the radiation imaging apparatuses 101a and 101b are mountable on a plurality of types of mounts will be described as an example. FIG. 5 is a schematic diagram illustrating an example of antenna initial value information stored in the storage unit 111 according to the present exemplary embodiment.

In the example illustrated in FIG. 5, the antenna ANT_1 is set as the initial antenna for the radiation imaging apparatus 101a mounted on the decubitus position-type mount 102, and the antenna ANT_2 is set as the initial antenna for the radiation imaging apparatus 101a mounted on the erect position-type mount 110. The antenna ANT_1 is also set as the initial antenna for the radiation imaging apparatus 101b mounted on the decubitus position-type mount 102, and as the initial antenna for the radiation imaging apparatus 101b mounted on the erect position-type mount 110. This structure provides for the antenna initial value information corresponding to the use condition being stored in the storage unit 111 for both of the radiation imaging apparatuses 101a and 101b. Employing such a configuration makes it possible to efficiently control the selection in correspondence with each use condition.

Next, a third exemplary embodiment will be described with reference to FIGS. 6 to 8.

Figure 6:
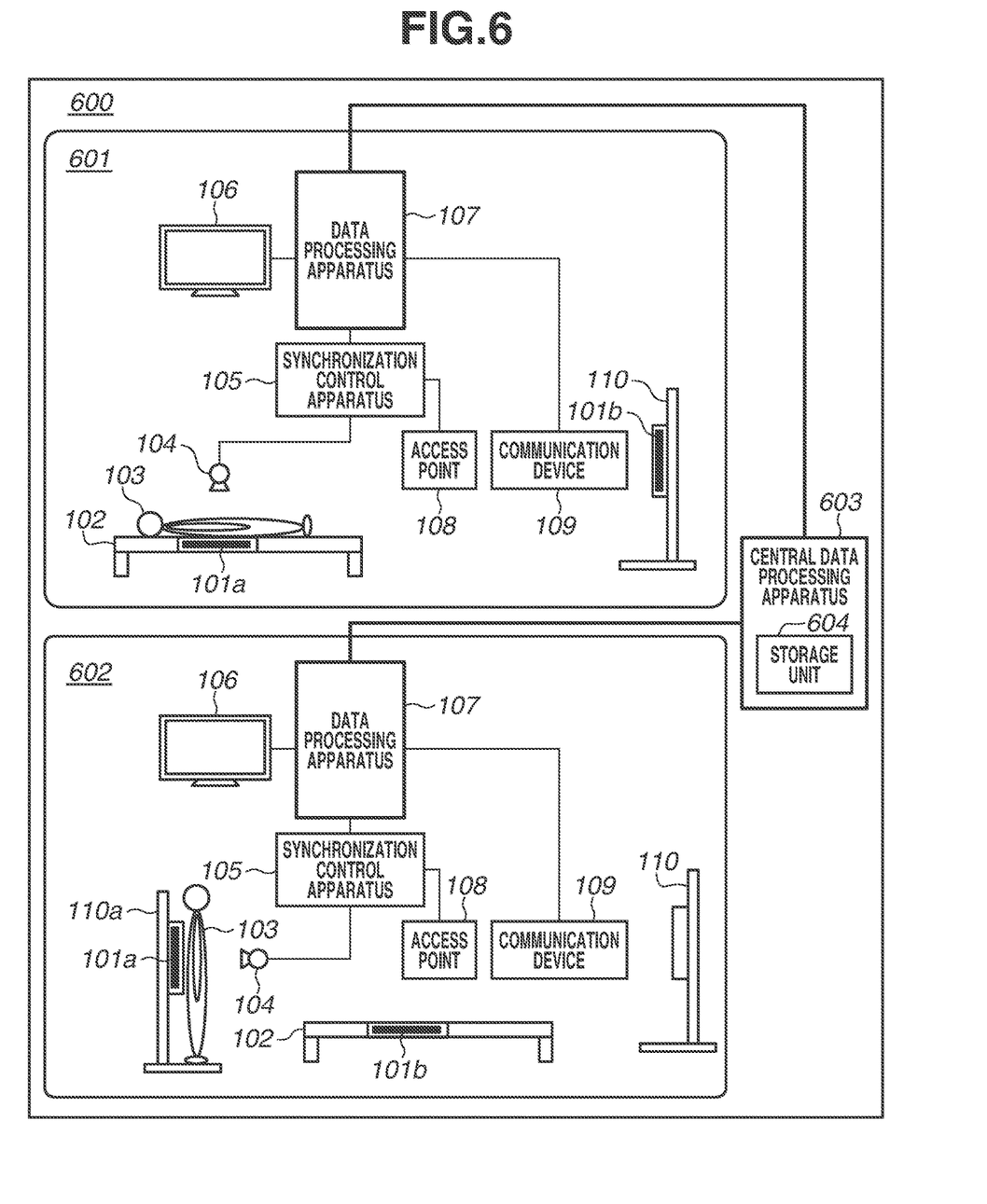
FIG. 6 is a block diagram illustrating a centralized management system according to a third exemplary embodiment.

FIG. 6 illustrates a centralized management system 600 that manages two radiation imaging systems 601 and 602. The centralized management system 600 connects the data processing apparatus 107 included in both of the radiation imaging systems 601 and 602 to a central data processing apparatus 603 in the centralized management system 600. The radiation imaging system 601 has the same configuration as that of the radiation imaging system 100 illustrated in FIG. 1, and the radiation imaging system 602 has a configuration in which an erect position-type mount 110a is added to the configuration of the radiation imaging system 100. In other words, the centralized management system 600 is configured such that the central data processing apparatus 603 functions as a data processing apparatus integral with the respective data processing apparatuses 107. The central data processing apparatus 603 includes a storage unit 604 storing the antenna initial value information for both of the radiation imaging systems 601 and 602, which is stored in the storage unit 111 of each of the data processing apparatuses 107.

Figure 7:
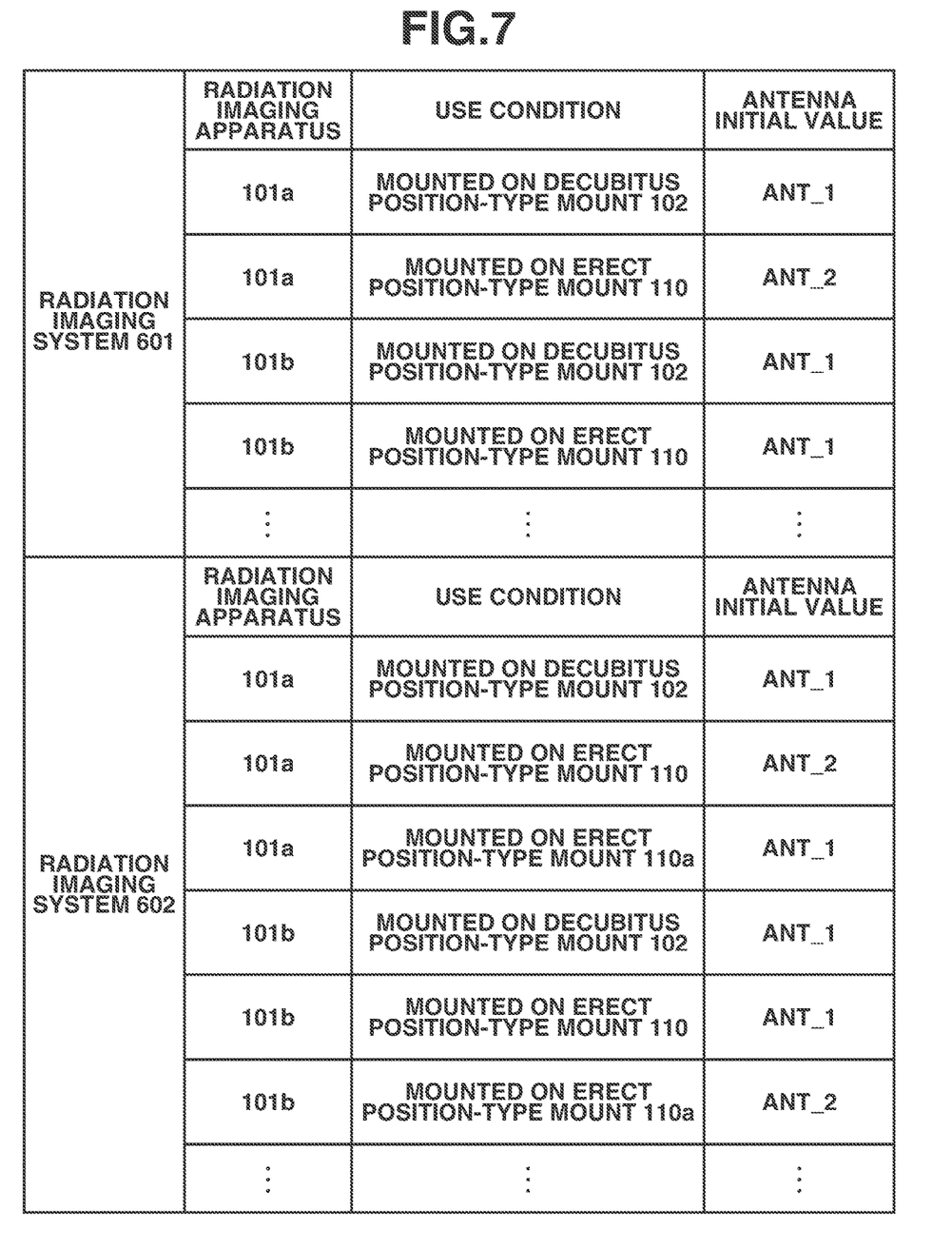
FIG. 7 is a schematic diagram illustrating an example of antenna initial value information according to the third exemplary embodiment.
Figure 8:
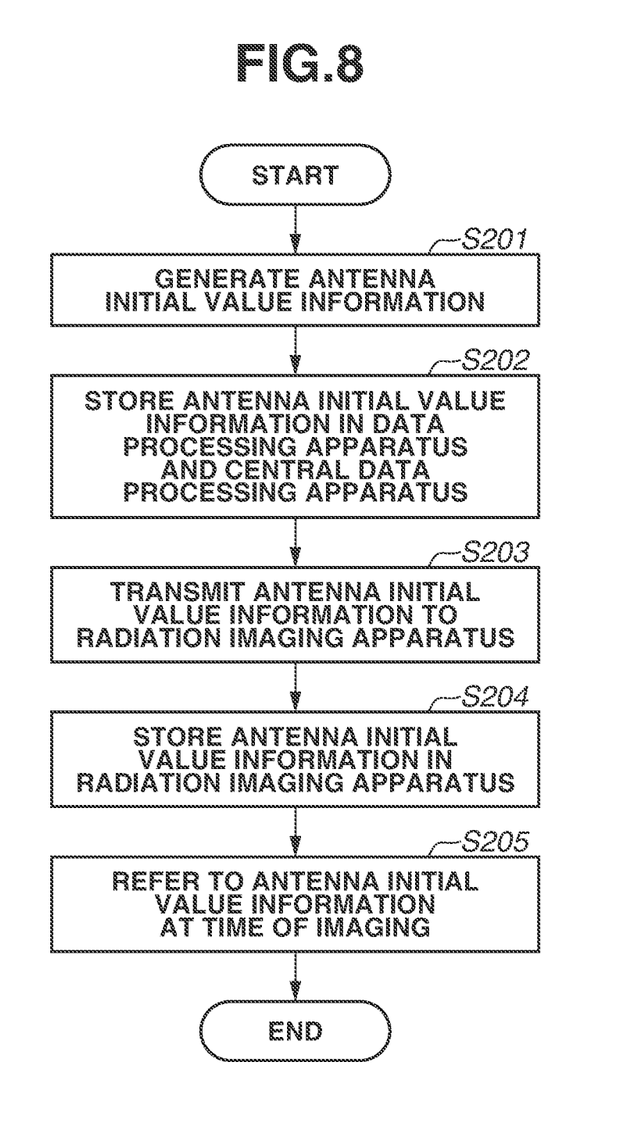
FIG. 8 is a flowchart illustrating selection control according to the third exemplary embodiment.

FIG. 7 is a schematic diagram illustrating a table of the antenna initial value information in the centralized management system 600, which is stored in the storage unit 604. The antenna initial value information is set for both of the radiation imaging systems 601 and 602, based on the radiation imaging apparatuses 101a and 101b included in each of the radiation imaging systems 601 and 602 and the use conditions thereof. For the radiation imaging system 601, the antenna initial value information is set with combinations of the radiation imaging apparatuses 101a and 101b and the decubitus position-type mount 102 and the erect position-type mount 110 as the use conditions. For the radiation imaging system 602, the antenna initial value information is set with combinations of the radiation imaging apparatuses 101a and 101b and the decubitus position-type mount 102, the erect position-type mount 110, and the erect position-type mount 110a as the use conditions. The antenna initial value information stored in the storage unit 604 is transmitted to the storage unit 111 of the data processing apparatus 107 in both of the radiation imaging systems 601 and 602 on a system-by-system basis, and is stored in the storage unit 111 in both of the radiation imaging systems 601 and 602.

Next, antenna selection control according to the present exemplary embodiment will be described with reference to the flowchart in FIG. 8. In step S201, the antenna initial value information illustrated in FIG. 3 is generated in the data processing apparatus 107. In step S202, the antenna initial value information is stored in the data processing apparatus 107 and, at the same time, is transmitted to the central data processing apparatus 603 and is stored in the storage unit 604 of the central data processing apparatus 603. At this time, the antenna initial value information is stored in the storage unit 604 for both of the radiation imaging systems 601 and 602 as illustrated in FIG. 7, and can be transmitted to the data processing apparatus 107 for use as backup data of the data processing apparatus 107. The antenna initial information can also be updated in the central data processing apparatus 603 and transmitted to the data processing apparatus 107 for use. In step S203, the antenna initial value information is transmitted from the data processing apparatus 107 to the radiation imaging apparatuses 101a and 101b. In step S204, the antenna initial value information is stored in the storage unit 211 of both of the radiation imaging apparatuses 101a and 101b. In step S205, the antenna initial information is referred to at the time of the imaging to control the antenna selection.

Each of the above-described exemplary embodiments can also be implemented by processing that supplies software (a program) for implementing the functions according to the above-described exemplary embodiments to a system or an apparatus via a network or a storage medium, and causes a computer (e.g., a central processing unit (CPU) or a micro processing unit (MPU)) of the system or the apparatus to read out and execute the program.

The above-described exemplary embodiments are not seen to be limiting, and can be changed and/or modified without departing from the spirit and the scope of the embodiments.

The exemplary embodiments provide a radiation imaging system that uses a radiation imaging apparatus configured to select an antenna to be used from a plurality of antennas for wireless communication, and that efficiently controls the selection.

OTHER EMBODIMENTS

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, these exemplary embodiments are not seen to be limiting. The scope of the following claims is to be accorded the broadest interpretation so as to encompass all such modifications and equivalent structures and functions.

This application claims the benefit of Japanese Patent Application No. 2021-031423, filed Mar. 1, 2021, which is hereby incorporated by reference herein in its entirety.

What is claimed is:

1. A radiation imaging system comprising:
a data processing apparatus; and
a radiation imaging apparatus including a plurality of antennas for performing, via wireless communication, at least one of reception of control data from the data processing apparatus or transmission of radiation image data to the data processing apparatus,
wherein the radiation image data is acquired by an imaging operation performed based on the control data and with respect to emitted radiation,
wherein the data processing apparatus transmits, to the radiation imaging apparatus, information about an antenna that is preset as an antenna to be used from among the plurality of antennas, and
wherein the radiation imaging apparatus selects, based on the information, the antenna to be used from the plurality of antennas.

2. The radiation imaging system according to claim 1,
wherein the data processing apparatus includes a storage unit storing the information, and
wherein, based on the information, the radiation imaging apparatus includes a first communication unit configured to perform at least one of the reception of the control data or the transmission of the radiation image data via the wireless communication, a second communication unit configured to receive the information, and a selection unit configured to select the antenna to be used from the plurality of antennas.

3. The radiation imaging system according to claim 2, further comprising a communication device configured to transmit the information from the data processing apparatus to the second communication unit via wireless communication.

4. The radiation imaging system according to claim 3, wherein the wireless communication between the communication device and the second communication unit is a different wireless communication than the wireless communication between the data processing apparatus and the first communication unit.

5. The radiation imaging system according to claim 3, wherein the wireless communication between the communication device and the second communication unit is short-range wireless communication.

6. The radiation imaging system according to claim 3, wherein the wireless communication between the communication device and the second communication unit is performed using a predetermined antenna among the plurality of antennas.

7. The radiation imaging system according to claim 2, wherein the storage unit stores the information corresponding to a use condition of the radiation imaging apparatus.

8. The radiation imaging system according to claim 2,
wherein the radiation imaging system comprises a plurality of the radiation imaging apparatuses, and
wherein the storage unit stores the information for each of the plurality of radiation imaging apparatuses.

9. A method for controlling a radiation imaging system comprising a data processing apparatus and a radiation imaging apparatus, the radiation imaging apparatus including a plurality of antennas for performing, via wireless communication, at least one of reception of control data from the data processing apparatus or transmission of radiation image data to the data processing apparatus, the radiation image data being acquired by an imaging operation performed based on the control data and with respect to emitted radiation, the method comprising:

causing the data processing apparatus to transmit, to the radiation imaging apparatus, information about an antenna that is preset as an antenna to be used from among the plurality of antennas; and     causing the radiation imaging apparatus to select, based on the information, the antenna to be used from the plurality of antennas.

10. A radiation imaging apparatus including a plurality of antennas for performing, via wireless communication, at least one of reception of control data from a data processing apparatus or transmission of radiation image data to the data processing apparatus, the radiation image data being acquired by an imaging operation performed based on the control data and with respect to emitted radiation, the radiation imaging apparatus comprising:

a communication unit configured to receive information about an antenna that is preset as an antenna to be used from among the plurality of antennas, the information being transmitted from the data processing apparatus; and     a selection unit configured to select, based on the information, the antenna to be used from the plurality of antennas.

11. A data processing apparatus configured to transmit control data to and receive radiation image data from a radiation imaging apparatus via wireless communication, the radiation imaging apparatus including a plurality of antennas for performing, via the wireless communication, at least one of reception of the control data or transmission of the radiation image data to the data processing apparatus, the radiation image data being acquired by an imaging operation performed based on the control data and with respect to emitted radiation, the data processing apparatus comprising:

a storage unit storing information about an antenna that is preset as an antenna to be used from among the plurality of antennas,     wherein the data processing apparatus transmits the information to the radiation imaging apparatus.

\* \* \* \* \*